United States Patent
Hofstraat et al.

(10) Patent No.: US 6,259,524 B1
(45) Date of Patent: Jul. 10, 2001

(54) PHOTOBLEACHABLE LUMINESCENT LAYERS FOR CALIBRATION AND STANDARDIZATION IN OPTICAL MICROSCOPY

(75) Inventors: Johannes Willem Hofstraat, Veldhoven; Godefriedus J. Brakenhoff; Rick I. Ghauharali, both of Amsterdam, all of (NL)

(73) Assignee: The University of Amsterdam (NL)

( * ) Notice: Subject to any disclaimer, the term of this patent is extended or adjusted under 35 U.S.C. 154(b) by 0 days.

(21) Appl. No.: 09/403,635
(22) PCT Filed: Apr. 17, 1998
(86) PCT No.: PCT/EP98/02358
  § 371 Date: Jan. 10, 2000
  § 102(e) Date: Jan. 10, 2000
(87) PCT Pub. No.: WO98/49537
  PCT Pub. Date: Nov. 5, 1998

(30) Foreign Application Priority Data

Apr. 25, 1997 (EP) .................................................. 97201235

(51) Int. Cl.[7] ........................................................ G01J 1/10
(52) U.S. Cl. ............................................. 356/243.4; 436/8
(58) Field of Search ................................ 356/243.1, 243.2, 356/243.3, 243.4, 243.5, 243.6; 436/8, 10, 19; 250/252.1

(56) References Cited

U.S. PATENT DOCUMENTS 4,055,376 * 10/1977 Daberko ............................. 356/243.4
4,868,126    9/1989 Schwartz ................................ 436/10

OTHER PUBLICATIONS

L.C. Smith et al., "Digital Imaging Fluorescence Microscopy", IEEE/Seventh Annual Conference of the Engineering in Medicine and Biology Society, (1985), pp. 967–970.

* cited by examiner

Primary Examiner—Hoa Q. Pham
(74) Attorney, Agent, or Firm—Knoble & Yoshida, LLC

(57) ABSTRACT

The invention pertains to a calibration layer comprising an optically transparent polymer containing an amount of photobleachable luminscent material present in such a way that the final polymer film contains less than 10 wt. % of luminophore and has an optical attenuation of less than 0.3 absorption units in the wavelength region of interest. The invention further is concerned with a method of calibration of an optical image device, preferably an optical or Raman microscope, by using the decrease in luminescence as the result of photobleaching between two consecutive images for calibration.

4 Claims, No Drawings

PHOTOBLEACHABLE LUMINESCENT LAYERS FOR CALIBRATION AND STANDARDIZATION IN OPTICAL MICROSCOPY

BACKGROUND OF THE INVENTION

The invention pertains to the preparation and use of thin, photobleachable luminescent layers for calibration and standardization of optical imaging devices, such as optical or Raman microscopy. For the quantitative application of optical and Raman microscopy, it is essential that the intensities in the images acquired with these microscopic techniques are determined only by the spatial distribution of the concentration, absorption, and emission characteristics of the luminophores in the specimen under investigation. If this is not possible, the image intensities should at least be proportional to these parameters. Generally, however, image intensity variations are not only determined by the specimen, but also by spatial non-uniformities of the optical system of the microscope across the field of view, so that only qualitative investigations can be performed. In order to realize the images required for quantitative microscopy, the microscope must be calibrated and standardized. The thus obtained images allow the comparison of different samples obtained on the same microscope, also at a different point in time, or the comparison of images obtained on different microscopes, provided that the different microscopes have been calibrated in the same way.

In earlier work, calibration and standardization of an optical microscope was attempted by an approach using images of a uniform luminescent layer (K. R. Castleman, *Digital Image Processing*. Prentice-Hall, Englewood Cliffs, N.J., 1979, and Z. Jericevic, B. Wiese, J. Brayan & L. C. Smith, "Validation of an Image System," in *Luminescence Microscopy of Living Cells in Culture, Part B, Quantitative Luminescence Microscopy- Imaging and Spectroscopy*, edited by D. Lansing Taylor and Y. Wang, Academic Press, San Diego, Calif., 1989). Such an approach has three disadvantages. Firstly, in the case of an image of a luminescent layer, the product of the illumination and detection efficiency distributions is measured, and no information on the separate distributions is available. Secondly, completely uniform luminescent layers are difficult to obtain. Thirdly, the results of calibration and standardization based on this approach are affected by luminescence photobleaching of the layer. For general calibration and standardization in optical microscopy, it would be preferable to have an approach which does not suffer from these disadvantages. Jericevic et al. (Z. Jericevic, B. Wiese, J. Brayan & L. C. Smith, "Validation of an Image System," in *Fluorescence Microscopy of Living Cells in Culture, Part B, Quantitative Fluorescence Microscopy-Imaging and Spectroscopy*, edited by D. Lansing Taylor and Y. Wang, Academic Press, San Diego, Calif., 1989) attempted to do away with the first disadvantage by using luminescence photobleaching techniques for the determination of only the illumination distribution. In his method, at least 20 images of a uniform, photobleaching luminescent layer were required. They showed that by numerically fitting the luminescence intensity decrease in each pixel of the first image with an exponential function, it was possible to determine only the excitation intensity distribution in the field of view of the used microscope (Z. Jericevic, D. M. Benson, J. Bryan, & L. C. Smith, "Rigorous Convergence Algorithm for Fitting a Monoexponential Function with a Background Term Using the Least-Squares Method," *Anal. Chem.*, 59 (1987), 658–662). There are several drawbacks to this method and experimental approach. Firstly, a luminescent layer has to be prepared by spreading an FITC-IgG mixture on a microscope slide. With such a procedure, it is very difficult to obtain a uniform luminescent layer. Secondly, the method provides only the illumination distribution; no information about the detection distribution is obtained. Thirdly, the determination of the illumination distribution is based on numerically fitting routines, which renders the method relatively slow.

BRIEF SUMMARY OF THE INVENTION

This invention describes the preparation and use of thin, photobleachable luminescent films for the calibration and standardization of an optical or Raman microscope in the wavelength region of 250 nm–1700 nm, preferably 250 nm–1100 nm, and more preferably 350 nm–900 nm.

DETAILED DESCRIPTION OF THE INVENTION

This is achieved according to the invention by the preparation of a photobleachable luminescent calibration layer and its subsequent use for the determination of excitation intensity and detection efficiency distributions in the field of view of the used microscope. The term photobleaching comprises all processes which result in the reduction of the intensity of luminescence light generated at the wavelength of excitation. Excitation may be done by laser or by a focused light source in the wavelength ranges defined above. Examples of such processes are photo-oxidation, photo-reduction, photo-isomerization or photo-addition reactions, or light-induced electron transfer processes.

It is sufficient for the effectiveness of the invention that the prepared calibration layer is approximately uniform, luminescent, and photobleachable, preferably approximately uniform, luminescent, and mono-exponentially photobleachable in a certain regime. The calibration layer should satisfy the following requirements.

(i) The luminescence intensity of luminophore in the calibration layer should be proportional to the excitation intensity, the luminophore concentration, and the illumination duration.

(ii) The rate of photobleaching of the luminophore in the calibration layer should be proportional to the illumination intensity and independent of the luminophore concentration.

(iii) The luminescence quantum yield, the absorption cross-section, and the bleach factor—defined as the ratio of the rate of photobleaching to the excitation intensity—of the luminophore in the calibration layer should be independent of the micro-environment within the layer.

The first two requirements already suffice for qualitative calibration of the measurement. The third requirement in combination with the first two allows absolute measurement of an image in optical or Raman microscopy.

The calibration layer is applied on an optically flat and transparent substrate by spin-coating, dip-coating or rod-coating (doctor blading) of a, preferably, 1–30 wt % solution of an optically transparent polymer containing an amount of photobleachable luminescent material present in such a way that the final polymer film contains less than 10 wt % of luminophore and has an optical attenuation of less than 0.3 absorption units in the wavelength region of interest, or of a solution of a sidechain polymer with an amount of photobleachable luminescent groups covalently attached to it, in such a way that the relative molar content of the sidechains is lower than 10% and the optical attenuation of the calibration layer is less than 0.3 absorption units in the wavelength region of interest. The useful concentration region is determined by the necessity to prevent intermolecular interactions (energy transfer) and inner filter and concentration quenching effects, which may lead to deviations tom simple mono-exponential decay. Optical attenuation more than 0.3 absorption units is possible, but mathematical corrections are required. Such attenuation is therefore less preferred. Suitable polymeric materials, which are transparent across the wavelength region of interest, are polyacrylates, polymethacrylates, polycarbonates, polyolefins, polyethers, polyurethanes, polyetherketones, polyesters, polystyrenes, polysiloxanes, and the like, or copolymers thereof. Suitable polymeric sidechain materials are based on the same optically transparent building blocks as applied in the transparent polymer types mentioned above and a suitable luminescent and photobleachable molecule which is equipped with a functional group so that it either may be attached to said polymer or may react with other functional monomers to form a luminescent sidechain-main chain polymer. Alternatively, thin films may be prepared by making use of sol-gel glass formation approaches.

The luminescent material used should be photobleachable, which means that the intensity of luminescence should be reduced by illumination in the microscope at the applied excitation wavelength. A number of light-induced processes may result in such photobleaching; some examples are photo-oxidation, photo-reduction, photo-isomerization or photo-addition reactions, or light-induced electron transfer processes. All luminescent photochromic materials may be used. The photobleachable luminescent material may undergo such change either reversibly or irreversibly.

In view of the excellent homogeneity of the luminescent layers obtained according to the above-mentioned procedure, even the direct luminescence intensity can be used for calibration.

With the prepared calibration layer, absolute excitation intensity and detection efficiency distributions in the field of view of the used microscope can be determined from images, before and after partial photobleaching, of the calibration layer and the luminescence quantum yield, the absorption cross-section, and the bleach factor of the luminophore in the calibration layer, as follows.

When the luminescence intensity of the calibration layer is proportional to the excitation intensity, the luminophore concentration, and the illumination duration, when its photobleaching is mono-exponential, and when its rate of photobleaching is proportional to the excitation intensity and independent of the luminophore concentration, an image of the layer acquired before any photobleaching has taken place, referred to below as the "first image," can be written as the product of the image exposure time, the luminescence quantum yield, the absorption cross-section, the bleach factor, and the concentration distribution of the luminophore in the calibration layer, and the excitation intensity and detection efficiency distributions of the used microscope. The detection efficiency includes all elements of the detection pathway important for the conversion of the intensity to be detected up to the intensity value of a pixel in the final image, such as the finite collection solid angle of the objective lens, the reflectivity and transmittance of the optical elements in the detection pathway, and the quantum efficiency of the detector. An image, referred to below as the "second image," acquired after the calibration layer has been bleached during a certain time interval, can be written as the product of the first image and an exponential function which is determined by the bleach factor, the excitation intensity, and the bleach time interval.

Based on these two images the relative excitation intensity distribution—or a distribution proportional to the excitation intensity distribution—in the field of view of the used microscope can be determined by calculating the logarithm of the ratio between the first and second images of the calibration layer. The absolute excitation intensity distribution can be determined by calculating the ratio of the relative excitation intensity distribution and the bleach factor of the luminophore in the calibration layer to the bleach time interval. It is important to point out that for the determination of this—relative or absolute—excitation intensity distribution, it is not required that the calibration layer is uniform.

Once the relative excitation intensity distribution has been determined, the relative detection efficiency distribution—or a distribution proportional to the detection efficiency distribution—can be determined as follows. Firstly, a distribution proportional to the product of the detection efficiency and luminophore concentration distributions, referred to below as the "product distribution," is determined by calculating the ratio of the first image to the relative excitation intensity distribution. Secondly, a number of product distributions are determined from the same number of image pairs, first and second images, with each image pair acquired from a different part of the calibration layer. By averaging these different product distributions, the contribution of possible non-uniformities of the luminophore concentration distribution can be eliminated, and a distribution proportional to only the detection efficiency distribution, i.e., the relative detection efficiency distribution, is obtained. The number of product distributions required for averaging depends on the uniformity of the calibration layer: for uniform layers, no averaging is required, but the less uniform the layer is, the larger the number of different product distributions should be. For many applications the determination of the relative distributions is already sufficient.

When the direct luminescence intensity is used, the excitation intensity distribution and the detection efficiency distribution cannot be determined separately. For many applications, e.g., shadow correction procedures, it is sufficient to use the product of the intensity distributions for calibration purposes.

The absolute detection efficiency distribution can be determined by calculating the product of the relative detection efficiency distribution, the bleach factor of the luminophore in the calibration layer, and the bleach time interval, and dividing the result by the image exposure time and the luminescence quantum yield, the absorption cross-section, and the mean luminophore concentration of the luminophore in the calibration layer. The parameters which have to be known for absolute determination of the excitation intensity and detection efficiency distributions are the absorption cross-section, the luminescence quantum yield, and the bleach factor of the calibration layer. All three parameters can be determined independent of the microscope used.

The absorption cross-section of the calibration layer at a certain wavelength can be determined by measuring the optical attenuation at the same wavelength and combining this information with the thickness of the layer and its luminophore concentration.

The luminescence quantum yield of the calibration layer can be determined through comparison of the luminescence of the calibration layer with the luminescence of a reference layer of which the luminescence quantum yield is known.

The bleach factor of the calibration layer can be determined by measuring the relative decrease of the luminescence intensity after illumination with a known excitation dose, i.e., energy per unit area.

With the excitation intensity and detection efficiency distributions known, a number of calibration and standardization steps in optical microscopy are available.

(i) The method can be employed to compare the excitation intensity and detection efficiency distributions of different microscopes, or of the same microscope at different points in time. Differences between the overall performance of microscopes can be attributed to the excitation pathway, the detection pathway or both. Such information can be used to selectively optimize the pathway that limits the performance. Another possibility is to adjust the illumination and detection parameters of different microscopes in such a way that equal—or at least comparable—excitation and detection conditions result This facilitates the comparison of measurements in which one (type of specimen is studied either with different microscopes or with the same microscope at different times.

(ii) The excitation intensity distribution is important in the interpretation of the intensity variations in images obtained with so-called luminescence bleach rate imaging (G. J. Brakenhoff, K. Visscher & G. Gijsbers, "Luminescence Bleach rate Imaging," *J. Microsc.*, 175 (1994), 154–161). in that imaging mode, the local rate of photobleaching rather than the luminescence intensity is used as a contrast parameter for image formation. Spatial non-uniformities of the excitation intensity distribution lead to—apparent—variations of the observed rate of photobleaching. With an experimentally determined excitation intensity distribution available, these apparent variations can be corrected.

(iii) The method can be used for the correction of intensity variations in an image of a specimen under investigation which are caused by non-uniformities of the optical system of the microscope, a procedure referred to as "shading correction." In the simple case of a luminescently labelled specimen of which the detected luminescence intensity is proportional to both the excitation intensity and the detection efficiency, shading correction is accomplished by calculating the ratio of the image of the specimen under investigation and the product of the—relative or absolute—excitation intensity and detection efficiency distributions. The fact that with the method, the excitation intensity and detection efficiency distributions are available separately implies that also in more complicated specimens, for example specimens in which non-linear dependencies occur, shading correction is possible.

(iv) The method can be employed for the quantitative investigation of specimens. The intensity variations in a shading corrected image of a specimen are independent of the microscope used to acquire the image and are determined only by specimen related factors such as the concentrations of the luminophores in the specimen and their absorption and emission characteristics. When shading correction is based on the absolute excitation intensity and detection efficiency distributions, the intensities in the shading corrected image of a specimen can be used to quantitatively determine these specimen related factors. For example, if a luminophore is available which can be used to luminescently label a specimen and if the luminescence quantum yield and the absorption-cross section of this luminophore are known and independent of the micro-environment within the specimen, the intensities in the shading corrected image can be used to quantitatively determine the concentration of this luminophore in the specimen on a microscopic level.

(v) The excitation intensity and detection efficiency distributions can be used for active image correction by modulating illumination and detection parameters during image acquisition in such a way that a spatially uniform illumination and detection efficiency results. This possibility is important for bleach rate imaging, photoactivatable processes, assessment of biological cell damage, etcetera.

EXAMPLES

To demonstrate the applicability of the invention, a luminescent and photobleachable calibration layer was prepared and used for shading correction of images acquired with a confocal luminescence microscope. The luminescent and photobleachable calibration layer was based on the luminophore 4-dimethylamino-4'-nitrostilbene (DANS). Solutions of DANS and polymethylmethacrylate (PMMA) in chloroform were prepared and used to spin-coat standard glass cover slips used for optical microscopy. For the investigation of the influence of the luminophore concentration on the luminescence intensity and the rate of photobleaching, three calibration layers were prepared with relative concentrations of 0.2, 0.5 and 1.0. DANS in PMMA can be excited in the wavelength range <250 nm–550 nm; it fluoresces in the wavelength range 500–850 nm. Upon irradiation, photobleaching of the fluorophore takes place, mainly due to photo-oxidation.

The microscope used for this demonstration was an Olympus IMT-2 inverted microscope (Olympus Corporation, Lake Success, N.Y., USA), equipped with an INSIGHT PLUS bilateral confocal line scanning unit (Meridian Instruments Inc., Okemos, Mich., USA) and a 100×, NA=1.32, oil immersion objective lens. Luminescence was excited at 488 nm, using an air cooled Argon ion laser (model 532, Omnichrome, Chino, Calif., USA). The excitation intensity could be varied by insertion of neutral density filters (NDFs) in the laser delivery path of the microscope. A total of four NDFs were available, with a transmittance ranging from 1% to 50%. The generated luminescence was detected with a cooled CCD camera (model DDE/3200, Astromed, Cambridge, UK) through a long-pass filter with a cut-off wavelength at 520 nm. A Hewlett-Packard model 725/50 workstation (Hewlett-Packard, Palo Alto, Calif., USA) was used for image collection and exposure control via a mechanical laser shutter. Image analysis was carried out on the same workstation, using the image processing package ScilImage (T. K. Ten Kate, R. van Balen, A. W. M. Smeulders, F. C. A. Groen & G. A. de Boer, "SCILIAM, a Multi-level Interactive Image Processing Environment," *Pattern Recognition Letters*, 11 (1990), 429–441).

For the investigation of the photobleaching characteristics of the calibration layer, so-called "bleach curves" were determined by acquiring a series of images—a time series—from a certain part of the calibration layer. The image exposure time was the same for all images in the time series, and no additional exposure occurred between successive images. From each time series, two quantities were determined: the mean initial luminescence intensity and the mean bleach rate. The mean initial luminescence intensity was calculated by averaging the intensities in the first image of the time series. The mean bleach rate should ideally be determined by averaging the bleach rates calculated for each pixel in the first image of the time series for a number of regions of interest (ROIs), which were chosen arbitrarily in the image. The data for each individual ROI were fitted with a (mono-) exponential function. The mean bleach rate was obtained as the mean of the individual ROI bleach rates.

For the luminescent layer it has been verified that its luminescence and photobleaching characteristics conform to the requirements of the method, i.e., the luminescence intensity in the first image of the calibration layer—or the initial luminescence intensity—should be proportional to the excitation intensity, the luminophore concentration, and the image exposure time, its photobleaching should be mono-exponential, and its rate of photobleaching should be proportional to the excitation intensity and independent of the luminophore concentration.

It was found that the conditions for the luminescence characteristics are satisfied by the proposed calibration layer. The photobleaching of the calibration layer initially was not strictly mono-exponential; however, close to mono-exponential photobleaching of the calibration layer could be realised by "pre-bleaching" the layer. The data obtained after 180 sec of pre-bleaching were used to calculate "the rate of photobleaching," which appeared to be proportional to the excitation intensity and independent of the luminophore concentration in the layer. Therefore, after suitable pre-bleaching, the requirements for the photobleaching characteristics are fulfilled by the prepared calibration layer.

The excitation intensity distribution can be determined from two images of the calibration layer, which are separated by a time interval in which the calibration layer is partially bleached. To calculate the relative excitation intensity distribution, the first and second images were acquired with a pre-bleaching time of 180 sec and a bleach time interval of 150 sec, since in this time-interval the decrease of the luminescence intensity is described well with a mono-exponential function. In these images, a stripe- and spot-like pattern can be seen, which is independent of the part of the calibration layer from which the images were acquired. This indicates that the stripe- and spot-like pattern is caused by non-uniformities of the optical system of the microscope. Inspection shows that the excitation intensity is not distributed uniformly over the image region, but that a stripe-like pattern occurs. It was found that this pattern is caused by the dichroic mirror in the microscope. The relative magnitude of the variations in excitation intensity over the image region can be expressed as the coefficient of variation (CV)—the ratio of the standard deviation to the mean. The measurement shows that in the relative—and absolute—excitation intensity distribution, variations of approximately 10% occur over the image region. The CV is a measure of the variation across the entire image. It should be pointed out that locally much larger variations can occur.

The detection efficiency distribution can also be determined from two images—the first and second images—of the calibration layer. The relative detection efficiency distribution is determined from the product distribution, which is proportional to the product of the detection efficiency and luminophore concentration distributions. The product distribution is determined from the first image of the calibration layer and the already determined relative excitation intensity distribution. By calculating the product distribution from different, randomly chosen, parts of the calibration layer and averaging the results, the relative detection efficiency distribution is obtained. By averaging a number of product distributions, measured at different parts of the calibration layer, the relative detection efficiency distribution is obtained. As already noted, this stripe-like pattern is caused by the dichroic mirror in the microscope, and since this mirror is part of both the excitation and detection pathway, the same pattern is visible in the relative excitation intensity and detection efficiency distributions. Also visible are dark spots which cannot be seen in the relative excitation intensity distributions. These are probably caused by small dust particles or other irregularities in the detection pathway of the microscope. The relative magnitude of the variations in detection efficiency can be estimated by again taking the CV as a measure of the variations. Variations of approximately 25% occurred in the relative—and absolute—detection efficiency distributions. Again, locally the variations can be much larger.

With the known relative excitation intensity and detection efficiency distributions shading correction of an image of a specimen can be carried out by calculating the ratio of the image of the specimen to the product of the relative excitation intensity and detection efficiency distributions.

Comparison before and after correction indicates a clear reduction of the intensity variations. Also visible is that a calibration layer feature—the deliberately photobleached line-shaped region—is well preserved after the correction procedure, whereas the intensity variations caused by the non-uniformities of the optical system have disappeared. A different way is to visualize the effect of the shading correction, in which case the intensities are plotted before and after correction. It is clear from this that the intensity variations after correction are significantly smaller than before correction. The effect of the shading correction was quantified by calculating the CV of the intensities in the images. The results show CVs of approximately 22% and 4% before and after correction, respectively. This means that the shading correction procedure achieved a more than five-fold decrease of the intensity variations. Locally the decrease of the image intensity variations obviously will be much larger.

What is claimed is:

1. A calibration layer comprising an optically transparent polymer containing a photobleachable luminescent material wherein the polymer contains less than 10 wt % of luminescent groups originating from the luminescent material and has an optical attenuation of less than 0.3 absorption units in the wavelength region of 250 to 1700 nm.

2. The calibration layer of claim 1 wherein a photobleachable luminescent group contained in the photobleachable luminescent material is covalently attached to a sidechain polymer the relative molar content of which is lower than 10%.

3. A method of calibration of an optical image device by:
   a. photobleaching the calibration layer of claim 1 as a series of images from different parts of the calibration layer;
   b. calculating the mean initial luminescence intensity and the mean bleach rate for each series;
   c. calculating a detection efficacy distribution from the data of b; and
   d. using the decrease in luminescence as the result of photobleaching between two subsequent images as a measure for calibration.

4. The method according to claim 3 wherein an optical or Raman microscope is calibrated.

* * * * *